United States Patent [19]

Sampathkumar et al.

[11] 4,333,872
[45] Jun. 8, 1982

[54] METHOD OF PRODUCING α-L-ASPARTYL-L-PHENYLALANINE METHYLESTER

[75] Inventors: Prathivadibhayankaram S. Sampathkumar, Parsippany; Basant K. Dwivedi, Randolph, both of N.J.

[73] Assignee: Chimicasa GmbH, Switzerland

[21] Appl. No.: 185,721

[22] Filed: Sep. 19, 1980

Related U.S. Application Data

[63] Continuation-in-part of Ser. No. 150,881, May 27, 1980, abandoned.

[51] Int. Cl.³ .......................................... C07C 103/52
[52] U.S. Cl. .............................................. 260/112.5 R
[58] Field of Search ................................. 260/112.5 R

[56] References Cited

U.S. PATENT DOCUMENTS 3,786,039  1/1974  Ariyoshi et al. ............. 260/112.5 R
3,830,792  8/1974  Tilak ............................ 260/112.5 R
3,879,372  4/1975  Boesten ....................... 260/112.5 R
3,901,871  8/1975  Anderson .................... 260/112.5 R
3,933,781  1/1976  Bachman et al. ............ 260/112.5 R

*Primary Examiner*—Delbert R. Phillips
*Attorney, Agent, or Firm*—Richard P. Crowley

[57] ABSTRACT

A method for preparing an α-L-aspartyl-L-phenylalanine alkyl ester, which method comprises: reacting a divalent alkali salt of aspartic acid, having an aminoprotective group, with an organic halo ester compound, to form a monovalent, alkali-salt, mixed,anhydride aspartate compound; and condensing the mixed,anhydride aspartate compound with an alkyl ester of L-phenylalanine under alkaline conditions and reducing the pH to an acidic condition after condensation to free the amino and carboxyl groups, to form a mixture consisting essentially of the alpha and beta alkyl ester of α-L-aspartyl-L-phenylalanine.

15 Claims, No Drawings

METHOD OF PRODUCING α-L-ASPARTYL-L-PHENYLALANINE METHYLESTER

REFERENCE TO PRIOR APPLICATION

This application is a continuation-in-part of U.S. Ser. No. 150,881, filed May 27, 1980, now abandoned, hereby incorporated by reference.

BACKGROUND OF THE INVENTION

The discovery of the sweetness of the dipeptide α-L-aspartyl-L-phenylalanine methylester was reported in 1969 by R. H. Mazur et al (Jour. Amer. Chem. Soc., 91, 2684, 1969). Since then, several methods have been developed for preparing the compound (see, for example, U.S. Pat. Nos. 3,475,403; 3,833,553; 3,798,206; 3,769,333; and 3,933,781).

In U.S. Pat. No. 3,475,403, Mazur et al react N-benzyloxycarbonyl-L-aspartic acid α-p-nitrophenol and β-benzylester and L-tyrosine methylester, to produce the β-benzyl-N-benzyloxycarbonyl-L-aspartyl-L-tyrosine methylester. In U.S. Pat. No. 3,933,781, L-phenylalanine and N-formyl-L-aspartic anhydride are used to form N-formyl-α-L-aspartyl-L-phenylalanine which is deformylated and then esterified to obtain the methylester compound.

The prior-art methods typically require a number of process steps and the use of various expensive reagents, resulting in a high cost for the α-L-aspartyl-L-phenylalanine dipeptide ester.

U.S. patent application Ser. No. 150,881, filed May 27, 1980, discloses the preparation of α-L-aspartyl-L-phenylalanine alkyl esters, particularly the methylester sweetener compound, in high yields; for example, over 70%, and without substantial racemization and isomer formation of the nonsweetener isomeric compound. The process comprises: reacting the free alpha-carboxyl group of an L-aspartate compound in which the β-carboxyl group and the amino group are blocked with the free amino group of an alkyl ester of L-phenylalanine, to provide an L-aspartyl-L-phenylalanine-coupled compound; and hydrogenating the coupled compound, to provide an α-L-aspartyl-L-phenylalanine alkyl ester.

SUMMARY OF THE INVENTION

The present invention relates to an improved method for the preparation of the sweetener α-L-aspartyl-L-phenylalanine methylester.

It has been found that α-L-aspartyl-L-phenylalanine alkyl esters, particularly the methylester sweetener compound, may be produced in high yields, without racemization and isomer formation of the nonsweetener isomeric compound, and at low cost.

We have discovered that the α-dipeptide alkyl esters, particularly the methylester representing the sweetener compound, can be obtained directly in good yield by reacting a divalent alkali metal salt of aspartic acid, wherein the amino group is protected, with a carboxyl blocking compound, such as a halo ester compound, to form a mixed alkali-ester, anhydride aspartate compound, and, thereafter, reacting, through a condensation reaction, the mixed anhydride aspartate compound with an alkyl ester of the L-phenylalanine or any amino-acid ester, to form the desired dipeptide, and particularly the methylester sweetener compound.

The method, firstly, comprises forming the divalent alkali salt of the L-aspartic acid typically by reacting an alkali hydroxide, such as an alkali metal hydroxide of potassium, sodium and lithium, for example, in an alcohol solution, such as a methanol, ethanol or other lower alkanol, with L-aspartic acid, and heating and refluxing the mixture, to form the divalent alkali salt of the L-aspartic acid. Particularly preferred is the reaction of the L-aspartic acid in a methanol-potassium hydroxide solution, to form the divalent potassium salt.

The amino group of the divalent alkali salt is protected by reacting one hydrogen of the amino group, typically in situ, after the formation of the divalent alkali salt, with an organic compound which would react with the hydrogen group. A wide variety of organic compounds may be employed to react with and protect the amino group. The amino-protective compound employed should be reacted, typically in situ, with the amino group, to protect the amino site from further reaction during the reaction with the halo ester to form the anhydride, and yet the amino-protective group should be removed easily after the condensation step through a reduction in pH to an acid pH or by hydrogenation, to reform the free-amino group and the free-carboxyl group of the desired aspartate. For example, the amino-group site may be protected by reaction with a carbobenzoxy halide, such as a carbobenzoxy chloride, as in the parent application. However, the use of this compound requires a separate hydrogenation step, as in the parent process. A preferred compound to protect the amino-group site is an alkyl acetoacetate compound, such as the methyl, ethyl and propyl acetoacetate.

The amino-protective divalent alkali salt of the aspartate is reacted with a halo ester in a quantity sufficient to displace one of the dialkali salt groups and to form the mixed alkali halo ester anhydride aspartate compound. The mixed anhydride aspartate compound thus provides for protection for both carboxyl groups-one by the alkali salt and one by the halo ester, and also protection for the amino group. Typically, the halo ester may comprise an alkyl; for example, $C_1$–$C_6$, halo; for example, chloro or bromo alkanoate, such as a $C_1$–$C_4$ alkanoate, with one preferred compound being an alkylchloroformate, such as a methyl, ethyl, propyl, chloro or bromoformate.

The mixed anhydride aspartate compound is then reacted in a condensation reaction carried out under alkaline conditions; for example, from about 8 to 9 pH, and at a low temperature; for example, below $-20°$ C., with an alkyl ester of the phenylalanine, and particularly the methylester where the desired sweetener compound is to be produced. The reaction mixture is then reduced in pH to an acidic pH of 2.0 or less, and typically 1.5 or less, to free the amino and carboxyl groups, thereby forming an alpha-beta mixture of the desired alkyl ester of the L-aspartyl-L-phenylalanine. The method provides for the direct formation of the alphabeta mixture of the dipeptide compound in good yield, without interfering by-products and at a low cost, through the use of lowcost reagents.

Thus, the method provides for the preparation of the desired α-dipeptide ester directly in good yield, by reacting the alkali salt of aspartic acid with the amino site protected, in situ, and reacting the mixed anhydride with L-phenylalanine methylester and subsequent deprotection by reduction of the pH, to free the amine. This method yields alpha and beta dipeptide esters simultaneously. The desired isomer formed of the dipeptide ester is formed preferentially in a larger yield, depending on the reaction conditions employed. Typically, such reaction conditions include carrying out the condensation reaction at a temperature of from −20° C. to −60° C.; for example, −30° C. to −40° C., and at a pH of from about 8 to 9, and typically 8.5 to 8.9 pH, with the subsequent regeneration of the free-amino and carboxyl groups by reducing the pH. The reaction mixture essentially is all alpha and beta dipeptide, with the alpha isomer having a larger yield. The undesired beta dipeptide ester can be separated readily from the alpha isomer by methods known in the art. The method does not require many steps and expensive reagents and is easily adapted for industrial application.

The process conditions of each step of the method may be varied. However, in the formation of the alkali ester of the aspartic acid, sufficient stoichiometric concentration of the monovalent alkali should be employed, to prepare the divalent alkali ester aspartate, and sufficient quantities of the amino-protective compound used to provide for protection of the amino group of the alkali aspartate compound. Thereafter, a sufficient stoichiometric amount of the halo ester should be employed, to react and displace one of the alkali salt groups, to form the monoalkali-monohalo ester, mixed,anhydride compound. Thereafter, the condensation reaction is carried out, using a stoichiometric concentration of the L-phenylalanine under alkaline conditions and low temperatures, and the subsequent reduction to free both the amino group and the carboxyl group to form the dipeptide.

The improved method of the invention is set forth in a general schematic sequence as follows:

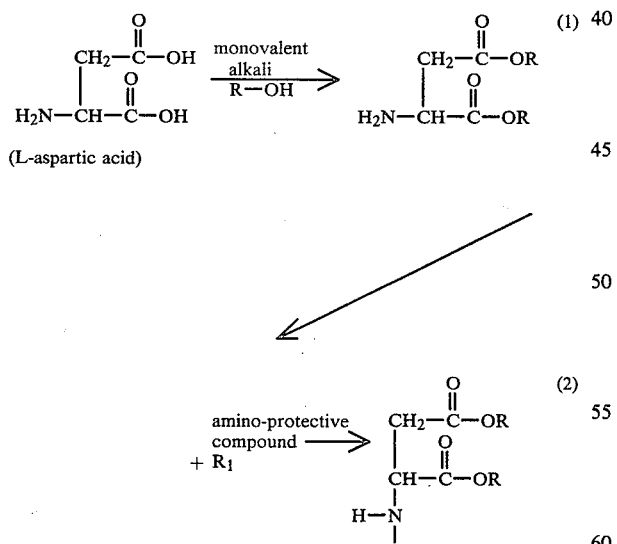

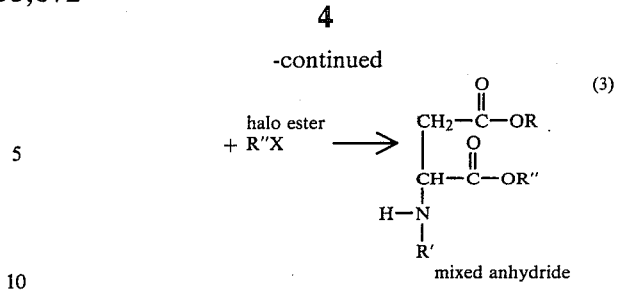

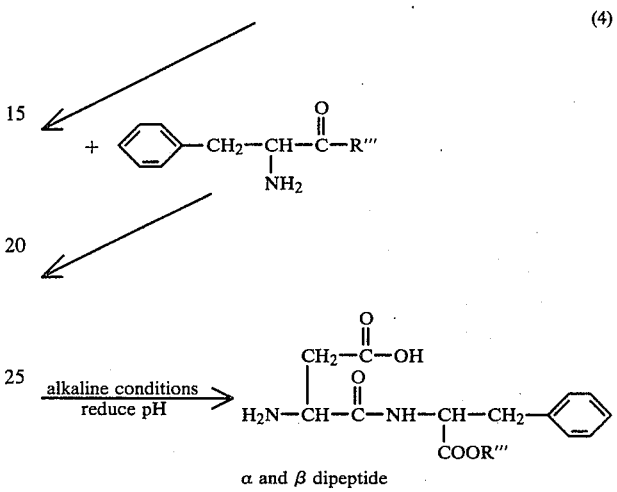

wherein R is a monovalent metal alkali; R' is an amino reactive compound; R'' is an ester group of halo ester; X is a halo group; and R''' is an alkyl group.

A preferred specific reaction sequence, employing a specific compound, is shown as follows:

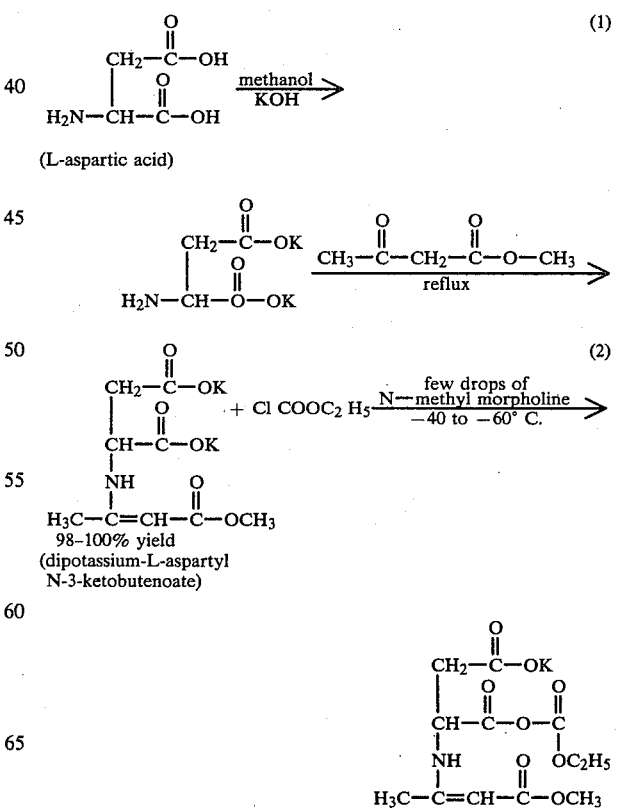

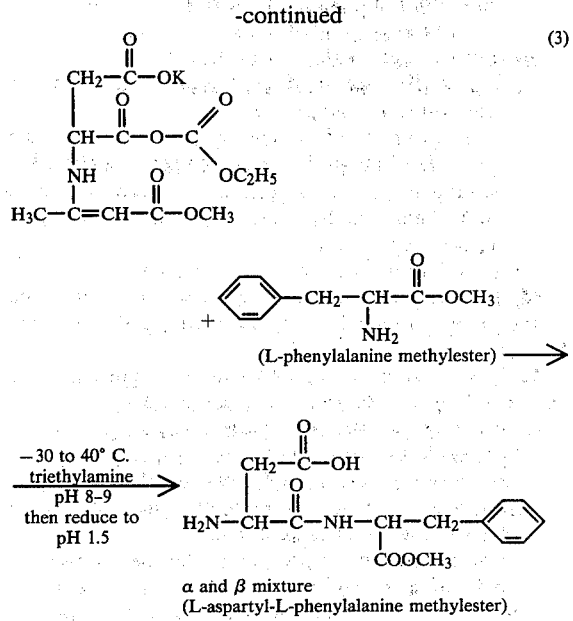

The method of the invention will be described in connection with certain preferred embodiments; however, it is recognized that those persons skilled in the art may make various changes and modifications in the embodiments shown, all within the spirit and scope of the invention.

DESCRIPTION OF THE EMBODIMENTS

EXAMPLE 1

Preparation of dipotassium-L-aspartyl N-3-ketobutenoate

A three-necked flask was charged with 360 ml of methanol (distilled over molecular sieves) and 44.8 g potassium hydroxide. The flask was attached with a condenser and a motored stirrer. The contents were heated with stirring to 45° C., when a clear solution was obtained. It was cooled to room temperature and 45.2 g of L-aspartic acid were added slowly with stirring. The contents were again refluxed for 15 minutes. It was cooled to room temperature, and 40.1 ml of methylacetoacetate in 197 ml of anhydrous methanol were slowly added and refluxed for ½ hour.

Methanol was stripped off completely under vacuum and the contents were added to 500 ml of 2-propanol. White precipitate was formed and was filtered off and dried in a vacuum desiccator over potassium hydroxide. Overall yield of this product was 97 to 98%.

EXAMPLE 2

Condensation of the potassium salt of L-aspartyl with the ester of phenylalanine 4.6 g of dipotassium-L-aspartyl N-3-ketobutenoate were added to a 500-ml three-necked flask attached with a stirrer, a thermometer and a calcium-chloride guard tube. Acetone (40 ml) was added and stirred at −55° C. for 10 minutes. Ethyl chloroformate (2.0 ml) was added while stirring, followed by 5 drops of N-methyl morpholine. Cooling was discontinued, and the temperature was allowed to rise to −30° C., and the mixture was stirred between −30° C. to −40° C. for 30 to 60 minutes, preferably 45 minutes. At the end of this period, it was cooled to −70° C. and filtered through a celite pad. The filtrate was kept at −55° C.

To the mixed anhydride maintained at −55° C., phenylalanine methylester hydrochloride (4.2 g) in 10 ml of water neutralized with triethylamine was added, and the pH was adjusted to 8.5 to 8.9. The contents were stirred at −40° C. to −30° C. for 1½ hours. At the end of the reaction period, 25 ml of water were added, followed by concentrated hydrochloric acid to bring the pH to 1.5, and the mixture was stirred at 0° C. for 10 minutes. The mixture was extracted with dichloromethane (2×70 ml), and the aqueous layer was adjusted to pH 4.1.

The resulting aqueous solution was chromatographed on a silica-gel column, to obtain pure α-L-aspartyl-L-phenylalanine methylester. A portion of the aqueous solution crystallized at 0° C., to give α-L-aspartyl-L-phenylalanine methylester.

The product was identified by melting point (235° C. to 36° C.), m. mpt and TLC comparison with an authentic commercial sample.

The yields of the α and β-isomers were qualitatively found to be 60:35 percent.

Having thus described our invention, what we claim is:

1. In a method for the preparation of an alkyl ester of α-L-aspartyl-L-phenylalanine which method comprises:
   condensing a monovalent alkali-ester mixed anhydride aspartate compound having an amino-protective group under alkaline condition with an alkyl ester of phenylalanine to produce an amino-protected ester condensate compound;
   the improvement which comprises:
   (a) providing an amino-protective group which is acid-removable with the ester group; and
   (b) reducing the pH of the amino-protected ester condensate compound to an acidic condition to remove the amino protective ester group and to form the alpha and beta mixture of the alkyl ester of α-L-aspartyl-L-phenylalanine.
2. The method of claim 1 which comprises reducing the pH to about 2.0 or less.
3. The method of claim 1 which includes separating the alpha isomer from the alpha and beta alkyl ester mixture.
4. The method of claim 1 wherein the acidremovable amino-protective group of the mixed anhydride aspartate compound is an alkyl acetoacetate group.
5. The method of claim 1 wherein the alkali salt is a potassium or sodium salt.
6. The method of claim 1 wherein the ester group of the mixed anhydride aspartate compound is an alkanoate group.
7. The method of claim 1 wherein the ester group of the mixed anhydride aspartate compound is an alkyl formate group.
8. The method of claim 1 wherein the alkyl ester is the methylester of phenylalanine to form the alpha and beta mixture of the methylester sweetener compound.
9. The method of claim 1 wherein the condensing step is carried out at an alkaline pH of from about 8 to 9 and at a temperature of about −20° C. to −60° C.
10. The method of claim 1 which includes forming the mixed aspartate compound by:
   (a) reacting aspartic acid with an alkali hydroxide to form the aspartate salt compound;

(b) reacting the aspartate salt compound with an acid-removable amino-protected compound, in situ, to form the amino-protected divalent alkali salt of aspartic acid; and
(c) reacting the amino-protected alkali salt of aspartic acid with an organic halo alkyl formate to form the monoalkali monoester mixed anhydride aspartate compound.

11. The method of claim 10 wherein the free amino group of the salt of the aspartic acid is reacted in situ, with an alkyl acetoacetate to form an amino protective group.

12. The method of claim 11 wherein the alkali hydroxide is potassium hydroxide, the alkyl formate is a chloro alkyl formate, and the alkyl acetoacetate is methyl acetoacetate.

13. In a method for the preparation of the methyl ester of α-L-aspartyl-L-phenylalanine which method comprises:

condensing a monovalent alkali-ester mixed anhydride aspartate compound having an amino-protective group under alkaline condition with the methyl ester of phenylalanine to produce an amino-protected ester condensate compound;

the improvement which comprises:
(a) providing an alkyl acetoacetate group as an amino-protective group;
(b) reducing the pH of the condensate compound to a pH of about 2.0 or less to remove the alkyl acetoacetate ester groups, and to form the alpha and beta methyl ester of α-L-aspartyl-L-phenylalanine; and
(c) recovering the alpha methyl ester.

14. The method of claim 13 wherein the ester group of the mixed anhydride aspartate compound is an alkyl formate group.

15. The method of claim 13 which includes forming the mixed anhydride aspartate compound by:
(a) reacting aspartic acid with a monovalent alkali hydroxide to form the aspartate salt compound;
(b) reacting the aspartate salt compound with an alkyl acetoacetate, in situ, to form the amino-protected alkali salt of aspartic acid; and
(c) reacting the amino-protected alkali salt of aspartic acid with an organic halo alkyl formate to form the monoalkali monoester mixed aspartate compound.

* * * * *